(12) United States Patent
Jeanne-Rose et al.

(10) Patent No.: US 8,680,212 B2
(45) Date of Patent: Mar. 25, 2014

(54) COMPOSITE DYESTUFF OF MICROCAPSULE TYPE AND COSMETIC USE THEREOF

(75) Inventors: Valérie Jeanne-Rose, Paris (FR); Ivan Rodriguez, Cauffry (FR)

(73) Assignee: L'Oreal, Paris (FR)

( * ) Notice: Subject to any disclaimer, the term of this patent is extended or adjusted under 35 U.S.C. 154(b) by 749 days.

(21) Appl. No.: 11/723,663

(22) Filed: Mar. 21, 2007

(65) Prior Publication Data
US 2007/0220686 A1    Sep. 27, 2007

Related U.S. Application Data

(60) Provisional application No. 60/790,775, filed on Apr. 11, 2006.

(30) Foreign Application Priority Data

Mar. 24, 2006    (FR) ...................................... 06 51031

(51) Int. Cl.
| | | |
|---|---|---|
| *C08G 63/48* | (2006.01) | |
| *A61K 8/73* | (2006.01) | |
| *A61K 8/87* | (2006.01) | |
| *C08G 63/91* | (2006.01) | |

(52) U.S. Cl.
USPC .............................. 525/438; 525/54.2; 8/406

(58) Field of Classification Search
USPC ............................................... 525/438, 54.2
See application file for complete search history.

(56) References Cited

U.S. PATENT DOCUMENTS

| 4,756,906 | A | * | 7/1988 | Sweeny .......................... 424/63 |
| 5,155,165 | A | * | 10/1992 | Maruyama et al. ........... 524/839 |
| 5,208,132 | A | * | 5/1993 | Kamada et al. ............... 430/138 |
| 5,597,557 | A | * | 1/1997 | Kumar et al. ............. 424/70.17 |
| 5,911,923 | A | | 6/1999 | Work et al. |
| 6,753,083 | B2 | | 6/2004 | Mistry et al. |
| 6,793,916 | B2 | * | 9/2004 | Toumi .............................. 424/69 |
| 6,890,653 | B2 | | 5/2005 | Wulff et al. |
| 2004/0232575 | A1 | * | 11/2004 | Wulff et al. .................... 264/4.1 |

FOREIGN PATENT DOCUMENTS

| GB | 1091141 | 11/1967 |
| WO | WO 03/101606 A1 | 12/2003 |
| WO | WO 2006/013165 A1 | 2/2006 |

OTHER PUBLICATIONS

Von Werner Siefken, "Mono-und Polyisocyanate," Justus Liebigs Annalen Der Chemie, 1948, 562. Band; pp. 75-136.

* cited by examiner

*Primary Examiner* — Janet Epps-Smith
*Assistant Examiner* — Audrea Buckley
(74) *Attorney, Agent, or Firm* — Oliff PLC

(57) ABSTRACT

The present invention relates to a composite dyestuff, characterized in that it is in the form of microcapsules composed of a polymer matrix of crosslinked polyurethane, polyurea and/or polyurethane/polyurea type obtained by interfacial polycondensation, and of a pigment.

14 Claims, 1 Drawing Sheet

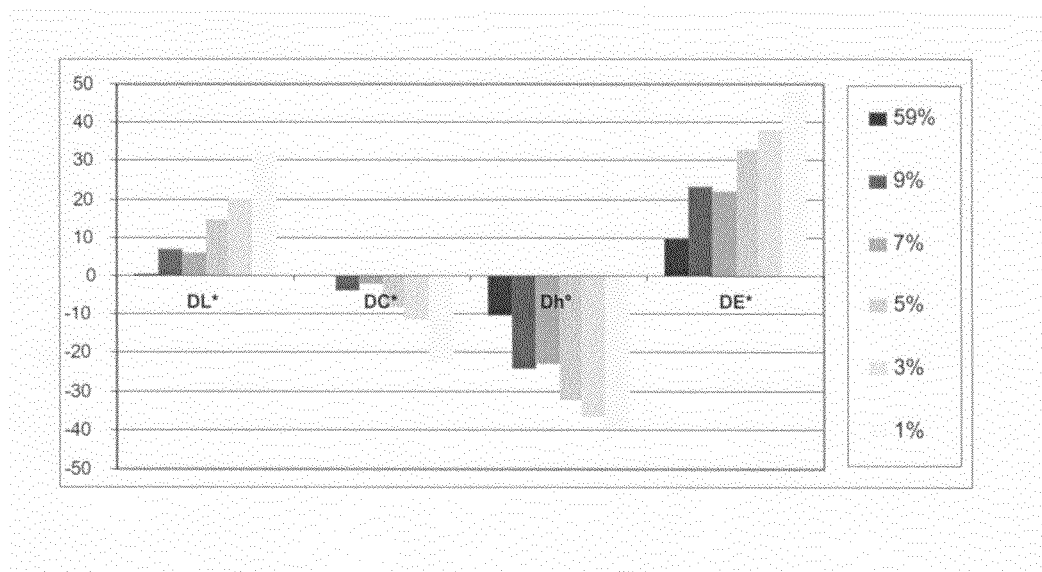

COMPOSITE DYESTUFF OF MICROCAPSULE TYPE AND COSMETIC USE THEREOF

This non provisional application claims the benefit of French Application No. 06 51031 filed on Mar. 24, 2006 and U.S. Provisional Application No. 60/790,775 filed on Apr. 11, 2006.

The present invention relates to composite dyestuffs in the form of microcapsules composed of a polymer matrix and comprising a pigment.

In general, the aim of cosmetic compositions is to afford an aesthetic effect, optionally in combination with a care effect, at the site of application for which they are intended. This aesthetic effect is, in the majority of cases, featured by a colour effect afforded by colouring substances present in the cosmetic composition.

As illustrations of compositions more particularly intended for generating a colour effect, examples that may be mentioned include lipsticks, foundations, eyeshadows, makeup rouges, eye pencils and mascaras.

Needless to say, the colouring substances that may be used for the manufacture of cosmetic and/or dermatological compositions intended for making up and/or caring for a keratin material should satisfy set standards in terms of harmlessness. Thus, there are in a certain number of countries lists in particular cataloguing the pigments whose use for makeup purposes is permitted.

These lists are restricting in many respects. Firstly, by permitting only a limited number of pigments, they do not afford access to a wide range of colours. Secondly, these lists differ according to the country concerned and therefore have only a small number of pigments in common. Consequently, the number of pigments that may be used over a wide economic region for making up a keratin material is relatively restricted.

There is thus a need to broaden the calorimetric range that is accessible from a given pigment, and especially from a pigment approved for a large economic area.

Moreover, it is known that certain pigments have a tendency to run. This running may lead to claw marks, for example on the lips (especially in the case of lipsticks) or on the nails (especially in the case of nail varnishes), and is thus reflected by impairment in the quality of the resulting makeup. Standard coating techniques (for example based on silicones or perfluoroalkyls) do not, unfortunately, make it possible to limit the observed running.

There is thus also a need to limit the running of pigments in water.

The present invention is specifically directed towards resolving these two aspects.

The inventors have discovered, surprisingly, that by encapsulating a pigment by interfacial polycondensation-crosslinking, an organic powder in which the said pigment is trapped can be obtained, making it possible, firstly, to gain access to colorimetric properties that are novel relative to the same pigment in free form, and, secondly, to overcome any problem of running.

Microencapsulation techniques are frequently used in the plant protection industry or in the self-copying paper industry.

Thus, document GB 1 091 141 discloses a process for encapsulating liquids by interfacial polymerization, leading especially to the formation of microcapsules formed from a crosslinked polymer matrix of polyamide, polyester, polyurea, polycarbonate or polyamide-polyurea type.

Patent U.S. Pat. No. 6,753,083 describes compositions that are useful for encapsulating various materials, and in particular catalysts, in a crosslinked or non-crosslinked polymer matrix, and which may be obtained by interfacial polymerization.

Finally, patents U.S. Pat. No. 6,890,653 and WO 03/101606 also disclose the encapsulation of water-soluble organic substances, for instance pheromones, in microcapsules formed from a polymer matrix of polyurethane and/or polyurea type, especially for the purpose of controlling their release.

However, none of these documents specifically applies such a technique to the encapsulation of a pigment in the field of cosmetics and especially for the purposes of broadening the colour range that is accessible from a single pigment.

Thus, according to a first of its aspects, the present invention relates to a composite dyestuff, characterized in that it is in the form of microcapsules composed of a polymer matrix of crosslinked polyurethane, polyurea and/or polyurethane/polyurea type and obtained by interfacial polycondensation, and of a pigment.

According to another of its aspects, the present invention relates to a cosmetic and/or dermatological composition, in particular for making up and/or caring for a keratin material, characterized in that it comprises at least one composite dyestuff according to the invention.

According to another of its aspects, the present invention relates to a cosmetic process for treating keratin materials, in particular bodily or facial skin, the nails, the hair and/or the eyelashes, comprising the application to the said materials of a cosmetic composition as defined above.

According to yet another of its aspects, the invention relates to the use of at least one composite dyestuff according to the invention for the preparation of a cosmetic composition for making up and/or caring for a keratin material.

Advantageously, the composite dyestuffs according to the invention have a different colour from that of the original pigment they contain, i.e. different from that of the pigment in non-encapsulated form.

In addition, since these composite dyestuffs are in the form of a powder, they may readily be used in all types of cosmetic composition, and under a wide range of operating conditions. The composite dyestuffs according to the invention may in particular be formulated in cosmetic products necessitating in the course of their manufacture a step of heating at high temperature, for instance lipsticks. They are thus advantageously distinguished from pigments in solution or in dispersion in a volatile solvent, or in a solvent capable of evaporating during the manufacturing process, or alternatively in a solvent that is incompatible with the other compounds.

The inventors have also discovered that the encapsulation of a pigment by interfacial polycondensation-crosslinking makes it possible to limit the running in water of the said pigment.

In the context of the present invention, the term "keratin material" denotes the skin, the lips, the nails, the hair, the eyelashes and the eyebrows, and the term "keratin fibres" more particularly denotes the hair, the eyelashes and the eyebrows.

The compositions according to the invention comprise a physiologically acceptable medium, especially a cosmetically acceptable medium, i.e. a medium that is compatible in particular with keratin materials, and especially keratin fibres such as the hair, the eyelashes and the eyebrows.

In the context of the present invention, the term "cosmetically acceptable" means a compound whose use is compatible with application to keratin materials and keratin fibres.

For the purposes of the invention, the microcapsules are particles of spherical shape consisting of a support material, also referred to as a "polymer matrix" in the present description, via which a pigment is trapped.

Polymer Matrix

The polymer matrices that are suitable for use in the present invention are of polyurethane, polyurea and/or polyurethane/polyurea type and are crosslinked.

According to one preferred embodiment of the invention, the polymer matrix of the microspheres according to the invention is of polyurethane/polyurea type.

The polymer matrix may be obtained by reacting at least two reagents, one of "isocyanate" type and the other of "alcohol and/or amine" type, at least one of these two reagents bearing at least three identical or different functions, chosen, for the first type, from isocyanate functions, and, for the second type, from hydroxyl and amine functions. This reagent especially ensures the crosslinking function.

According to a first embodiment variant, the polymer matrix may be obtained, for example, by reacting a reagent of alcohol and/or amine type comprising at least three identical or different functions chosen from hydroxyl and amine functions, with a reagent of isocyanate type comprising only one, or preferably even two, isocyanate function(s).

According to another embodiment variant, the polymer matrix may also be obtained by reacting a triisocyanate or a polyisocyanate with a reagent of alcohol and/or amine type comprising only one, or preferably even two, function(s), which may where appropriate be identical or different, chosen from hydroxyl and amine functions.

Water may also act as a reagent and generate an amino group, by addition to an NCO group and consecutive removal of $CO_2$, the said amino group then possibly reacting in situ with an NCO group.

Reagents of Isocyanate Type

The reagents of isocyanate type that may be used to form the composite dyestuffs according to the invention may comprise one or more, and especially two, or even three isocyanate functions. They may be chosen, for example, from aliphatic, cycloaliphatic, araliphatic, aromatic and heterocyclic di- or polyisocyanates such as those described, for example, by W. Siefken in Justus Liebigs Annalen der Chemie, 562, pages 75 to 136.

According to one embodiment of the invention, the reagents of isocyanate type may be chosen from diisocyanates, and especially ethylene diisocyanate, 1,4-tetramethylene diisocyanate, 1,6-hexamethylene diisocyanate, 2,2,4- or 2,4,4-trimethyl-1,6-hexamethylene diisocyanate, 1,12-dodecane diisocyanate, cyclobutane 1,3-diisocyanate, cyclohexane 1,3- and 1,4-diisocyanate, and any mixture of the isomers thereof, 4,4'-methylenebis(cyclohexyl)diisocyanate, 1-isocyanato-3,3,5-trimethyl-5-isocyanatomethyl-cyclohexane, 2,4- and 2,6-hexahydrotolylene diisocyanate and any mixture of the isomers thereof, hexahydro-1,3- and 1,4-phenylene diisocyanate, perhydro-1,4'- and 4,4'-diphenylmethane diisocyanate, 1,3- and 1,4-phenylene diisocyanate, 2,6-tolylene diisocyanate and any mixture of the isomers thereof, 4,4'-diphenylmethane diisocyanate (4,4'-MDI), 1,5-naphthylene diisocyanate, m-xylylene diisocyanate, tetramethylxylylene diisocyanate, m- and p-isocyanatophenylsulfonyl isocyanates, lysine alkyl ester diisocyanate in which the alkyl is of $C_1$ to $C_{10}$, or 2-butyl-2-ethylpentamethylene diisocyanate, and mixtures thereof.

According to another embodiment of the invention, the reagents of isocyanate type may comprise at least three isocyanate functions and may thus act as crosslinking agents. They may then be chosen especially from triisocyanates, for instance triphenyl-methane 4,4',4"-triisocyanate, or 4-isocyanatomethyl-1,8-octanemethylene diisocyanate, or alternatively from polyisocyanates, and especially polyphenylpolymethylene polyisocyanates, perchlorinated polyisocyanates, polyisocyanates containing carbodiimide groups, polyisocyanates containing allophanate groups, polyisocyanates containing isocyanurate groups, polyisocyanates containing acylated urea groups, polyisocyanates containing bis-urea groups, polyisocyanates prepared by telomerization reaction, polyisocyanates containing ether groups, the products of reaction of the isocyanates mentioned above with acetals, polyisocyanates containing polymeric fatty acid radicals, and any mixture of the polyisocyanates mentioned above.

It is also possible to use, as reagent of isocyanate type, mixtures of the said isocyanates, i.e. mixtures of aliphatic isocyanates, mixtures of aromatic isocyanates, mixtures of aliphatic and aromatic isocyanates, and in particular mixtures optionally comprising modified diphenylmethane diisocyanates.

Illustrations of these mixtures that may especially be mentioned include biuret of hexamethylene diisocyanate mixed with 4,4'-diphenylmethane isocyanate, and optionally with 2,4-diphenylmethane isocyanate, trimerized hexamethylene diisocyanate, mixed with 4,4'-diphenylmethane diisocyanate, and optionally with 2,4-diphenylmethane diisocyanate.

It is also possible to use, as reagent of isocyanate type, oligo- or polyisocyanates that may be prepared from the di- or polyisocyanates mentioned above or mixtures thereof by bonding them using urethane, allophanate, urea, bis-urea, amide, isocyanurate, carbodiimide, uretonimine, oxadiazinetrione or iminooxadiazinedione structures.

Mention may also be made of di- or polyisocyanates, such as mixtures of diphenylmethane diisocyanate monomers and of diphenylmethane diisocyanate oligomers (also known as MDI polymers), 2,4-tolylene diisocyanate (2,4-TDI), 2,4'-diphenylmethane diisocyanate (2,4'-MDI), triisocyanatotoluene, isophorone diisocyanate (IPDI), 2-butyl-2-ethylpentamethylene diisocyanate, 2-isocyanatopropylcyclohexyl isocyanate, 3(4)-isocyanatomethyl-1-methylcyclohexyl isocyanate, 1,4-diisocyanato-4-methylpentane, 2,4'-methylenebis(cyclohexyl) diisocyanate and 4-methylcylcohexane 1,3-diisocyanate (H-TDI), which may be used more particularly as reagent of isocyanate type.

Thus, according to one preferred embodiment, the reagents of isocyanate type that may be used to form the composite dyestuffs according to the invention are chosen from di- or polyisocyanates and especially mixtures of diphenylmethane diisocyanate monomers and of diphenylmethane diisocyanate oligomers (MDI polymers), tolylene diisocyanate (TDI), and especially 2,4-tolylene diisocyanate and 2,6-tolylene diisocyanate, and also the mixture thereof, 4,4'-diphenylmethane diisocyanate (4,4'-MDI), or isophorone diisocyanate (IPDI).

The amount of reagent of isocyanate type to be used for the implementation of the invention varies within the range usually used in interfacial polyaddition processes, and depends in particular on the desired degree of microencapsulation.

Reagents of Alcohol and/or Amine Type

The reagents of alcohol and/or amine type that may be used to form the composite dyestuffs according to the invention may comprise one or more, and especially two, or even three, identical or different functions chosen from hydroxyl and amine functions.

They may be chosen, for example, from reagents of alcohol type, reagents of amine type and reagents of amino alcohol type, used alone or as mixtures.

They preferably have a molecular weight ranging from 200 to 4000 g/mol.

Reagents of Alcohol Type

The reagents of alcohol type that may be used to form the composite dyestuffs according to the invention may comprise one or more, and especially two, or even three, hydroxyl functions.

More particularly, these reagents may be a polyol.

For the purposes of the invention, the term "polyol" means any organic molecule comprising in its chemical structure at least two hydroxyl groups —OH.

The polyol may be, for example, a linear, branched or cyclic, saturated or unsaturated hydrocarbon-based compound bearing at least two hydroxyl functions.

The polyol may in particular be a (hydro)carbon-based compound preferably containing from 2 to 300 carbon atoms, and bearing at least two hydroxyl groups and preferably from 2 to 10 hydroxyl groups.

Preferably, it is a (hydro)carbon-based compound containing from 3 to 32 carbon atoms, especially from 4 to 18 carbon atoms or even from 4 to 12 carbon atoms.

In particular, the polyol may be a compound containing from 2 to 18 carbon atoms and from 2 to 6 hydroxyl functions.

According to one embodiment of the invention, the reagents of alcohol type may be chosen from diols and especially glycol derivatives such as diethylene glycol, dipropylene glycol, ethylene glycol, propylene glycol, hexylene glycol, isoprene glycol, butylene glycol and pentylene glycol, or butanediol, 1,2-propanediol, pentanediols and in particular 1,5-pentanediol, decanediol and dodecanediol, or mixtures thereof.

According to another embodiment of the invention, the reagents of alcohol type may comprise at least three hydroxyl functions, and may thus act as crosslinking agents. They may then be chosen especially from trimethylolpropane, glycerol, pentaerythritol, 1,2,3-trihydroxyhexane, erythritol, arabitol, adonitol, dulcitol and sorbitol, glycerol polymers and copolymers, for instance hexaglycerol and diglycerol, glycerol derivatives, for instance butyldiglycol, polyglyceryl-3 diisostearate and castor oil, glycol derivatives, for instance polyethylene glycols and especially polyethylene glycols (PEG) containing from 4 to 150 ethylene glycol units, for instance PEG-400, PEG-600, PEG-800 and PEG-1200, polypropylene glycols, copolymers of ethylene glycol and of propylene glycol, or alternatively sugars such as glucose, fructose, xylose, trehalose, sucrose, maltose and lactose, and mixtures thereof.

Preferably, the reagents of alcohol type that are useful for acting as crosslinking agent are chosen from trimethylolpropane, glycerol, pentaerythritol and sugars.

The polyol may also be a polyether alcohol with an average molecular weight ranging from 150 to 600, such as polyethylene glycol 300 and polyglycerol 500.

It is also possible to use any mixture of the polyols mentioned above.

The polyol may also be chosen from non-etherified polyols and non-esterified polyols.

According to one preferred embodiment, the reagents of alcohol type that may be used to form the composite dyestuffs according to the invention are chosen from diols, for instance diethylene glycol, polyols, for instance polyethylenes glycols, and especially those containing from 4 to 150 ethylene glycol units, or alternatively mixtures of polyethylene glycols and of diethylene glycol.

Reagents of Amine Type

The reagents of amine type that may be used to form the composite dyestuffs according to the invention may comprise one or more, and especially two, or even three amine functions.

According to one advantageous embodiment of the invention, the reagents of amine type may be chosen from diamines, for instance diaminoethane, diaminopropanes, diaminobutanes, diaminohexanes, piperazine, 2,5-dimethylpiperazine, amino-3-amino-methyl-3,5, 5-trimethylcyclohexane (isophorone diamine, IPDA), 4,4'-diaminodicyclohexylmethane, 1,4-diaminocyclohexane, aminoethylethanolamine, hydrazine or hydrazine hydrate.

According to another embodiment of the invention, the reagents of amine type may comprise at least three amine functions, and may thus act as crosslinking agent. They may then be chosen especially from triamines, for example guanidine, diethylenetriamine or 1,8-diamino-4-aminomethyloctane.

The reagents of amine type may also be used in the form of ketimines, ketazines or corresponding amine salts.

According to one preferred embodiment, the reagents of amine type that may be used to form the composite dyestuffs according to the invention comprise at least one amino group chosen from primary amine and secondary amine groups of NHR type, in which R represents an alkyl group containing from 1 to 8 carbon atoms.

The reagents of amine type are preferably soluble in water in their native form, or in the form of a salt thereof.

Reagents of Amino Alcohol Type

The reagents of amino alcohol type that may be used to form the composite dyestuffs according to the invention may comprise at least two different functions chosen from amine and hydroxyl functions.

According to one embodiment of the invention, the reagents of amino alcohol type may be difunctional, i.e. they may comprise two functions, namely an amine function and a hydroxyl function.

According to another embodiment of the invention, the reagents of amino alcohol type may comprise at least three functions, and may thus act as crosslinking agents. They may comprise, for example, a single hydroxyl (or, respectively, amine) function and at least two amine (or, respectively, hydroxyl) functions, or alternatively two hydroxyl (or, respectively, amine) functions and at least one amine (or, respectively, hydroxyl) function.

As reagents of amino alcohol type that may be used in the present invention, mention may be made especially of ethanolamine and triethanolamine.

As mentioned previously, the polymer matrices of the microcapsules according to the invention may, according to a first alternative, be obtained by reacting at least one diisocyanate, for example as described above, with at least one reagent of alcohol and/or amine type bearing at least three identical or different functions, chosen from hydroxyl and amine functions, and acting as crosslinking agent, optionally in the presence of at least one diol and/or of at least one diamine and/or of at least one difunctional amino alcohol as described above.

According to one preferred embodiment, the reagent of isocyanate type is a diisocyanate chosen from mixtures of diphenylmethane diisocyanate monomers and of diphenylmethane diisocyanate oligomers (MDI polymers), tolylene diisocyanate (TDI) and especially 2,4-tolylene diisocyanate and 2,6-tolylene diisocyanate, and also a mixture thereof, 4,4'-diphenylmethane diisocyanate (4,4'-MDI), or alternatively isophorone diisocyanate (IPDI).

Examples of reagents acting as crosslinking agent that may be used include the triols, polyols, triamines and polyamines described previously.

According to one preferred embodiment, the reagent acting as crosslinking agent is chosen from triols, for instance trimethylolpropane, glycerol and pentaerythritol, and polyols, for instance sugars such as glucose, fructose, xylose, trehalose, sucrose, maltose and lactose.

According to one preferred embodiment, the diamines comprise at least one amino group chosen from primary amine and secondary amine groups of the type —NHR, in which R represents an alkyl group containing from 1 to 8 carbon atoms.

The polymer matrices according to the invention are especially obtained by interfacial polycondensation of at least two reagents as described above.

Interfacial polycondensation is a polymerization reaction that takes place at the interface of two immiscible liquids, at least one of the two containing a suitable polyfunctional reagent.

According to one preferred embodiment, at least one monomer and/or reagent is soluble in the first phase and at least one monomer and/or reagent is soluble in the second phase, which is immiscible with the said first phase.

When this reaction takes place without removal of side products, it is also known as interfacial polymerization.

This reaction may especially be performed in an emulsion, especially a two-phase or even a multi-phase emulsion, at the interface between the immiscible phases.

In the context of the present patent application, the reaction may be performed in an emulsion of oil-in-water or water-in-oil type, or alternatively in a multiple emulsion of water-in-oil-in-water or oil-in-water-in-oil type.

According to one preferred embodiment, the emulsion is of the oil-in-water type.

As mentioned previously, the polymer matrices that are suitable for use in the present invention are crosslinked.

This crosslinking is obtained by reacting the polymer chains with a reagent with a functionality at least equal to 3, known as a crosslinking agent, examples of which are given above.

Following the crosslinking of the polymer matrix, the effects induced on the pigment encapsulated according to the invention, and, for example, the modification of the shade, are irreversible.

Depending on the structure of the polymer matrix, two types of microcapsule are distinguished:
  microcapsules of matrix type, also known as microspheres, in which the polymer matrix is a continuous network, in which the pigment to be encapsulated is dispersed,
  microcapsules of reservoir type in which the polymer matrix is a solid envelope, also known as a "shell", of variable thickness, delimiting a core in which the pigment to be encapsulated is trapped.

In the context of the present invention, the microcapsules of reservoir type can trap the said pigment in their shell and/or in their core.

When the reaction is performed in an emulsion, and if the oligomers formed at the start of the reaction are insoluble in the dispersed phase, the formation of microcapsules of reservoir type is favoured. On the other hand, if the said oligomers are soluble in the dispersed phase, the formation of microcapsules of matrix type is then favoured.

When the polymerization is performed in the absence of solvent, the microcapsules obtained are of matrix type.

When the polymerization is performed in the absence of solvent but in the presence of an oil, especially a cosmetic oil, which does not solvate the oligomers formed, the microcapsules obtained are of reservoir type.

According to one embodiment of the invention, the microcapsules are of reservoir type.

According to another embodiment, the pigment according to the invention is trapped in the shell of the microcapsules of reservoir type.

According to another embodiment, the pigment according to the invention is trapped in the core of the microcapsules of reservoir type.

The pigment according to the invention may also be trapped both in the shell and in the core of the microcapsules of reservoir type.

According to another embodiment of the invention, the microcapsules are of matrix type.

According to the present invention, and without further precision, the term "microcapsules" is intended to cover both microcapsules of matrix type and microcapsules of reservoir type.

The microcapsules according to the invention have a size of between 500 nm and 1200 μm and especially between 500 nm and 30 μm.

The size of the microcapsules may be measured, for example, by optical or electronic microscopy, or by laser granulometry.

Pigments

The term "pigment" is intended to denote a white or coloured solid particle, which is naturally insoluble in the liquid hydrophilic and lipophilic phases usually used in cosmetics, or which is made insoluble by formulation in the form of a lake, where appropriate.

The term "pigment" may for example denote a white or coloured solid particle, which is insoluble in an isododecane solution when it is present therein in a content of 10% by weight, relative to the total weight of said solution, at 25° C. and at 1 atm.

The term "insoluble" is intended to denote, for the purpose of the invention, that suspended particles remain in the liquid phase, and in particular in the isododecane solution, or that the mixture is not limpid after mixing and stirring during 30 minutes.

In the context of the present invention, the pigment may be at least partly organic.

According to one embodiment of the invention, the pigment is an organic pigment.

According to another embodiment of the invention, the pigment is a mineral pigment.

The microcapsules according to the invention comprise not more than 80% by weight of pigment relative to the weight of the polymer matrix. In particular, they may comprise from 10% to 80% by weight, for example from 15% to 75% by weight, especially from 20% to 70% by weight or even from 25% to 65% by weight and in particular from 30% to 60% by weight of the pigment relative to the weight of the polymer matrix.

The expression "relative to the weight of the polymer matrix" is intented to denote that the corresponding content refers only to the weight of the polymer matrix, without taking into account the pigment.

In other words, it means that the corresponding content refers to the total weight of the monomer(s) entering in the composition of the polymer matrix.

Needless to say, the degree of encapsulation depends on the desired modification of the shade and may thus vary significantly according to the effect that it is desired to obtain.

As illustrations of pigments that may be used in the present invention, mention may be made of carbon black, titanium oxide, chromium oxide, pigments of D&C or FD&C type and lakes thereof, and especially those known under the names D&C Blue No. 4, D&C Brown No. 1, FD&C Green No. 3, D&C Green No. 5, D&C Green No. 6, FD&C Green No. 8, D&C Orange No. 4, D&C Orange No. 5, D&C Orange No. 10, D&C Orange No. 11, FD&C Red No. 4, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, FD&C Red No. 40, FD&C Red 40 lake, D&C Violet No. 2, Ext. D&C Violet No. 2, FD & C Blue No. 1, D&C Yellow No. 6, FD&C Yellow No. 6, D&C Yellow No. 7, Ext. D&C Yellow No. 7, D&C Yellow No. 8, D&C Yellow No. 10 or D&C Yellow No. 11, it being understood that when the said pigment is not naturally insoluble in the hydrophilic and lipophilic phases usually used in cosmetics, it is used in the form of a corresponding lake.

Examples of lakes that may especially be mentioned include lakes based on barium, strontium, calcium or aluminium, or alternatively diketopyrrolopyrroles.

As further examples of pigments that may be used in the present invention, mention may be made especially of mineral pigments, optionally surface-treated and/or coated, and especially titanium dioxide, zirconium oxide or cerium oxide, and also zinc oxide, iron oxide (black, yellow or red) or chromium oxide, manganese violet, ultramarine blue, chromium hydrate and ferric blue, or alternatively metal powders, for instance aluminium powder, copper powder, gold powder and silver powder.

Mention may also be made of pigments with an optical effect such as particles comprising a natural or synthetic organic or mineral substrate, for example glass, acrylic resins, polyester, polyurethane, polyethylene terephthalate, ceramics or aluminas, the said substrate being optionally covered with metal substances, for instance aluminium, gold, silver, platinum, copper or bronze, or with metal oxides, for instance titanium dioxide, iron oxide or chromium oxide.

They may also be nacres.

The term "nacres" should be understood as meaning iridescent particles, which are especially produced by certain molluscs in their shell, or alternatively which are synthesized.

The nacreous pigments may be chosen from mica coated with titanium or with bismuth oxychloride, titanium mica coated with iron oxides, titanium mica coated especially with ferric blue or with chromium oxide, titanium mica coated with an organic pigment of the abovementioned type, and also nacreous pigments based on bismuth oxychloride. Interference pigments, especially liquid-crystal or multilayer pigments, may also be used.

They may also be pigments having a structure that may be, for example, of sericite/brown iron oxide/titanium dioxide/silica type.

They may also be pigments having a structure that may be, for example, of silica microsphere type containing iron oxide.

As examples of pigments and lakes that are most particularly suitable for use in the present invention, mention may be made especially of D&C Red No. 7, titanium oxide, chromium oxide, lakes of the pigments of D&C and FD&C type mentioned above, and especially D&C Red No. 22 lake, Yellow No. 6 lake and FD&C Blue No. 1 lake.

Other Non-Colouring Substances

The composite dyestuffs according to the invention may also additionally comprise at least one non-colouring substance, which may be chosen from cosmetic oils and waxes, especially mineral, animal, plant or synthetic oils and waxes, cosmetic active agents such as vitamins, UV-screening agents, fragrances and moisturizers.

The additional non-colouring substance may be trapped in the shell or in the core of the microcapsule, when this microcapsule is of reservoir type, independently of the location of the pigment.

The additional non-colouring substance may be present in the microcapsules according to the invention in a content ranging from 0.001% to 60% by weight relative to the weight of the polymer matrix.

In particular, the additional cosmetic oils may be present in the microcapsules according to the invention in a content ranging from 10% to 60% by weight relative to the total weight of the polymer matrix.

The additional cosmetic active agents may be present in a content ranging from 0.001% to 10% by weight relative to the total weight of the polymer matrix.

The size of the microcapsules may be advantageously controlled by adding a minimum amount of a hydrophobic oil, which is preferably hydrocarbon-based, for instance isododecane, or Parleam, and/or of fatty acid esters, especially of fatty alkyl benzoate, in an amount ranging especially from 5% to 20% by weight relative to the total weight of the polymer matrix.

The composite dyestuffs according to the invention may be obtained by interfacial polycondensation, and more particularly via the following preparation process.

This process may be performed at a temperature ranging from 0° C. to 100° C. Emulsification of the aqueous phase and of the organic phase is obtained by stirring, for example using a homogenizer of Ultra-Turrax® type or a sonicator (ultrasound probe) at a temperature ranging from 2° C. to 40° C. and preferentially of about 15° C.

After emulsification, the water-soluble comonomers are introduced into the aqueous phase and the temperature of the reaction medium is raised to a temperature ranging from 60° C. to 100° C. and preferentially of about 65° C., in order to initiate the polymerization.

According to the invention, the polymerization may be performed in the presence or absence of a catalyst, for instance tin 2-ethylhexanoate.

At the end of polymerization, the powder may be recovered by centrifugation (4000 rpm for 30 minutes) or by filtration, or optionally by lyophilization. The powder thus obtained is then washed with water and with ethanol, and then air-dried.

The aqueous phase generally consists of water, but may also be an aqueous solution containing a water-soluble organic solvent.

The aqueous phase may also contain stabilizers, colloids, for instance polyvinyl alcohol (PVA) or a polyvinylpyrrolidone (PVP), and ionic surfactants, for example sodium lauryl sulfate (SDS), or nonionic surfactants, for instance polyethylene oxide-polypropylene oxide-polyethylene oxide block copolymers of the Pluronic range.

It may also contain the water-soluble monomer(s).

The organic phase contains the hydrophobic monomer(s) (reagents of isocyanate type) and the pigment.

It may contain a solvent for the isocyanate monomers, such as toluene, xylene, or a volatile oil (isodocane) or non-volatile mineral oil (Parleam, alkyl benzoate), or plant, animal or silicone oil (dimethylsiloxane or phenyl silicone) or a wax, or a mixture of these oils and waxes. The organic phase may also contain an agent for dispersing the pigment (Solsperse®).

The composite dyestuffs according to the invention may be used in cosmetics and/or dermatology especially for colouring and/or opacifying a cosmetic and/or dermatological composition.

Thus, according to one of its aspects, the invention relates to a cosmetic and/or dermatological composition, in particular for making up and/or caring for a keratin material, characterized in that it comprises at least one composite dyestuff according to the invention.

A composition according to the invention may comprise from 0.01% to 50% by weight, especially from 0.1% to 20% by weight and in particular from 0.5% to 15% by weight, relative to its total weight, of composite dyestuff as defined above.

The cosmetic or dermatological compositions according to the invention comprise, besides the said composite dyestuff, a physiologically acceptable medium, especially a cosmetically or pharmaceutically acceptable medium, i.e. a medium that is compatible with keratin materials such as facial or bodily skin, the lips, the hair, the eyelashes, the eyebrows and the nails.

The compositions according to the invention may thus comprise, depending on the intended application, constituents that are common for this type of composition.

Thus, the compositions according to the invention may comprise a hydrophilic medium comprising water or a mixture of water and of hydrophilic organic solvent(s), for instance alcohols and especially linear or branched lower monoalcohols containing from 2 to 5 carbon atoms, for instance ethanol, isopropanol or n-propanol, and/or polyols, for instance glycerol, diglycerol, propylene glycol, sorbitol, pentylene glycol and polyethylene glycols; and/or hydrophilic $C_2$ ethers and $C_2$-$C_4$ aldehydes; and/or short-chain esters (containing from 3 to 8 carbon atoms in total) such as ethyl acetate, methyl acetate, propyl acetate, n-butyl acetate or isopentyl acetate.

The compositions according to the invention may advantageously comprise a liquid fatty phase, which may itself comprise oils and/or solvents, which are preferably lipophilic; waxes, gums and/or pasty fatty substances, of plant, animal, mineral or synthetic origin, which may even be silicone-based, and mixtures thereof.

As waxes that may be present in a composition according to the invention, examples that may be mentioned, alone or as a mixture, include hydrocarbon-based waxes such as beeswax; carnauba wax, candelilla wax, ouricury wax, Japan wax, cork fibre wax or sugarcane wax; paraffin wax, lignite wax; microcrystalline waxes; lanolin wax, Montan wax; ozokerites; polyethylene waxes; waxes obtained by Fischer-Tropsch synthesis; hydrogenated oils, fatty esters and glycerides that are solid at 25° C. It is also possible to use silicone waxes, for instance alkyl or alkoxy polymethylsiloxanes and/or polymethyl-siloxane esters.

The compositions according to the invention may also comprise volatile or non-volatile, carbon-based, hydrocarbon-based, fluoro and/or silicone oils of mineral, animal, plant or synthetic origin, alone or as a mixture, provided that they form a homogeneous and stable mixture and that they are compatible with the intended use.

As oils that may be present in a composition according to the invention, mention may especially be made, alone or as a mixture, of hydrocarbon-based oils such as liquid paraffin or liquid petroleum jelly; perhydrosqualene; arara oil; sweet almond oil, beauty-leaf oil, palm oil, castor oil, avocado oil, jojoba oil, olive oil or cereal germ oil; lanolic acid, oleic acid, lauric acid or stearic acid esters; alcohols such as oleyl alcohol, linoleyl alcohol, linolenyl alcohol, isostearyl alcohol or octyldodecanol. Silicone oils may also be mentioned, such as optionally phenylated polydimethylsiloxanes, for instance phenyl trimethicones.

The compositions according to the invention may also comprise volatile oils, such as cyclotetradimethylsiloxane, cyclopentadimethylsiloxane, cyclohexadimethyl-siloxane, methylhexyldimethylsiloxane, hexamethyldisiloxane or isoparaffins.

Preferably, the composition according to the invention comprises at least one oil chosen from volatile isoparaffins such as isododecane, carbon-based non-volatile oils such as Parleam or alkyl benzoate, polydimethylsiloxanes, volatile silicones and phenyl silicone oils.

The compositions according to the invention may also comprise one or more additional dyestuffs, which may be chosen from water-soluble dyes, liposoluble dyes, and pulverulent dyestuffs, for instance pigments, nacres and flakes that are well known to those skilled in the art.

These additional dyestuffs may be present in the composition in a content ranging from 0.01% to 50% by weight and preferably from 0.02% to 25% by weight relative to the weight of the composition.

The term "additional pigments" should be understood as meaning white or coloured, mineral or organic particles of any form, which are insoluble in the physiological medium, and which are intended to colour the composition. As mineral pigments that may be used as additional pigments, mention may be made especially of titanium dioxide, optionally surface-treated, zirconium oxide or cerium oxide, and also zinc oxide, iron oxide (black, yellow or red) or chromium oxide, manganese violet, ultramarine blue, chromium hydrate and ferric blue, and metal powders, for instance aluminium powder or copper powder.

As organic pigments that may be used as additional pigment, mention may be made especially of carbon black, pigments of D&C type, and lakes based on cochineal carmine or on barium, strontium, calcium or aluminium.

The nacreous pigments may be chosen from white nacreous pigments such as mica coated with titanium or with bismuth oxychloride, coloured nacreous pigments such as titanium mica coated with iron oxides, titanium mica coated especially with ferric blue or with chromium oxide, titanium mica coated with an organic pigment of the abovementioned type and also nacreous pigments based on bismuth oxychloride.

Water-soluble dyes that may especially be mentioned include the disodium salt of ponceau, the disodium salt of alizarin green, the trisodium salt of amaranth, the disodium salt of tartrazine, the monosodium salt of rhodamine, the disodium salt of fuchsin, xanthophyll and methylene blue.

The compositions according to the invention may also comprise one or more fillers, especially in a content ranging from 0.01% to 50% by weight and preferably ranging from 0.02% to 30% by weight relative to the total weight of the composition.

The term "fillers" should be understood as meaning colourless or white, mineral or synthetic particles of any shape, which are insoluble in the medium of the composition irrespective of the temperature at which the composition is manufactured. These fillers serve especially to modify the rheology or the texture of the composition. The fillers may be mineral or organic and of any shape, platelet-shaped, spherical or oblong, irrespective of the crystallographic form (for example lamellar, cubic, hexagonal, orthorhombic, etc.).

Examples of fillers that may especially be mentioned include talc, mica, silica, kaolin, polyamide (Nylon®) powder (Orgasol® from Atochem), poly-β-alanine powder and polyethylene powder, powders of tetrafluoroethylene polymers (Teflon®), lauroyllysine, starch, boron nitride, hollow polymer microspheres such as those of polyvinylidene chloride/acrylonitrile, for instance Expancel® (Nobel Industrie), powders of acrylic acid polymers (Polytrap® from the company Dow Corning) and silicone resin microbeads (for example Tospearls® from Toshiba), elastomeric polyorganosiloxane particles, precipitated calcium carbonate, magnesium carbonate, magnesium hydrogen carbonate, hydroxyapatite, hollow silica microspheres (Silica Beads® from Maprecos), glass or ceramic microcapsules, and metal soaps derived from organic carboxylic acids containing from 8 to 22 carbon atoms and preferably from 12 to 18 carbon atoms, for example zinc stearate, magnesium stearate, lithium stearate, zinc laurate or magnesium myristate.

The compositions according to the invention may also comprise ingredients commonly used in cosmetics, such as vitamins, thickeners, gelling agents, trace elements, softeners, sequestrants, fragrances, acidifying or basifying agents, preserving agents, sunscreens, surfactants, antioxidants, hair-loss counteractants, antidandruff agents, propellants, ceramides, cosmetic active agents, moisturizers, vitamins, essential fatty acids, polymers, stabilizers and colloids, or mixtures thereof.

Needless to say, a person skilled in the art will take care to select this or these optional additional compound(s), and/or the amount thereof, such that the advantageous properties of the composition according to the invention are not, or are not substantially, adversely affected by the envisaged addition.

The compositions according to the invention may especially be in the form of a suspension, a dispersion, a solution, especially an organic solution, a gel, an emulsion, especially an oil-in-water (O/W) or water-in-oil (W/O) or multiple emulsion (W/O/W or polyol/O/W or O/W/O), in the form of a cream, a paste, a mousse, a vesicular dispersion, especially of ionic or nonionic lipids, a two-phase or multi-phase lotion, a spray, a powder or a paste, especially a soft paste.

The composition may be anhydrous, for example it may be an anhydrous paste.

For the purposes of the present invention, the term "anhydrous" means a composition comprising less than 5% by weight of water and especially less than 3% by weight of water, or even which is free of water.

A person skilled in the art may select the appropriate galenical form, and also the method for preparing it, on the basis of his general knowledge, taking into account, firstly, the nature of the constituents used, especially their solubility in the support, and, secondly, the intended application of the composition.

The compositions according to the invention may be makeup compositions, especially a complexion product such as a foundation, a makeup rouge or an eyeshadow; a lip product such as a lipstick or a lipcare product; a concealer product, a blusher, a mascara, an eyeliner, an eyebrow makeup product, a lip or eye pencil; a nail product such as a nail varnish or a nailcare product; a body makeup product or a hair makeup product (hair mascara or hair lacquer).

The compositions according to the invention may be compositions for protecting or caring for facial skin, the neck, the hands or the body, especially an anti-wrinkle or anti-fatigue composition for making the skin look radiant, a moisturizing or treating composition; an antisun or artificial tanning composition.

The compositions according to the invention may also be hair products, especially for the care, hygiene or maintenance of the hairstyle or for shaping the hair. The hair compositions are preferably shampoos, gels, hairsetting lotions, blow-drying lotions, or fixing and styling compositions such as lacquers or sprays. The lotions may be conditioned in various forms, especially in vaporizers or pump-dispenser bottles, or in aerosol containers so as to allow application of the composition in vaporized form or in mousse form. Such conditioning forms are indicated, for example, when it is desired to obtain a spray or a mousse for fixing or treating the hair.

The compositions according to the invention may also be hair colouring compositions.

Advantageously, the compositions according to the invention may be makeup compositions, especially for the nails or the lips. In particular, they may constitute a nail varnish or a lipstick.

A subject of the invention is also a cosmetic process for treating keratin materials, especially facial or bodily skin, the nails, the hair and/or the eyelashes, comprising the application to the said materials of a cosmetic composition as defined above.

The examples and figures presented below are presented as non-limiting illustrations of the field of the invention.

FIG. 1: Colorimetric differences between non-encapsulated DC Red 7 and DC Red 7 encapsulated according to the invention, at different pigment contents.

EXAMPLE 1

Synthesis of Microcapsules Comprising 57.5% by Weight of D&C Red No. 7 Relative to the Weight of the Polymer Matrix An oil-in-water emulsion is prepared comprising an organic phase consisting of 24 g of 4,4'-diphenylmethane diisocyanate (or MDI) in which are dispersed 20 g of D&C Red No. 7 (LCW) to be encapsulated, and 45 g of isododecane, and a continuous aqueous phase consisting of 800 g of water in which are dissolved 8 g of ethylene glycol, 2.8 g of trimethylolpropane and 1.7 g of sodium dodecyl sulfate (or SDS).

A protective colloid of 98% hydrolysed PVA polyvinyl alcohol type (Mw=13 000-23 000) may be added to a proportion of 5% by weight, relative to the aqueous phase, according to the desired particle size.

The emulsification is performed at high shear using an Ultra-Turrax® blender (between 6000 and 27 000 rpm) or a sonicator (between 10% and 90% amplitude).

The polymerization is performed at 63° C. in the presence or absence of tin 2-ethylhexanoate (catalyst) for 4 hours and then at room temperature for 15 hours.

At the end of reaction, the powder is recovered by filtration or by centrifugation.

EXAMPLE 2

Synthesis of Microcapsules Containing 1% by Weight of D&C Red No. 7 Relative to the Weight of the Polymer Matrix An oil-in-water emulsion is prepared comprising an organic phase consisting of 12 g of 4,4'-diphenylmethane diisocyanate in which are dispersed 0.18 g of D&C Red No. 7 and 2.8 g of isododecane, and a continuous aqueous phase consisting of 400 g of water in which is dissolved 5% of 98% hydrolysed PVA (Mw=13 000-23 000) and 0.84 g of Pluronic F68®. After emulsifying for 40 minutes with an Ultra-Turrax blender (13 500 rpm), 4 g of diethylene glycol and 1.38 g of trimethylolpropane are introduced.

The polymerization is performed at 63° C. for 4 hours and then at room temperature for 15 hours.

At the end of reaction, the powder is recovered by centrifugation (4000 rpm for 30 minutes).

The microcapsules obtained are characterized as being of reservoir type by observation with a scanning electron microscope.

EXAMPLE 3

Synthesis of Microcapsules Comprising 3% by Weight of D&C Red No. 7 Relative to the Weight of the Polymer Matrix The synthetic protocol is identical to that described in Example 2, using 0.52 g of D&C Red No. 7 (instead of 0.18 g).

EXAMPLE 4

Synthesis of Microcapsules Comprising 7% by Weight of D&C Red No. 7 Relative to the Weight of the Polymer Matrix The synthetic protocol is identical to that described in Example 2, using 1.22 g of D&C Red No. 7 (instead of 0.18 g).

EXAMPLE 5

Synthesis of Microcapsules Comprising 57% by Weight of D&C Red No. 7 Relative to the Weight of the Polymer Matrix An oil-in-water emulsion is prepared comprising an organic phase consisting of 24 g of 4,4'-diphenylmethane diisocyanate in which are dispersed 20 g of D&C Red No. 7 and 245.4 g of Parleam® and a continuous aqueous phase consisting of 800 g of water in which are dissolved 5% by weight of 98% hydrolysed PVA (Mw=13 000-23 000). After emulsification for 40 minutes using an Ultra Turrax® blender (13 500 rpm), 8 g of ethylene glycol and 2.76 g of trimethylolpropane are introduced.

The polymerization is performed at 63° C. for 4 hours and then at room temperature for 15 hours.

At the end of reaction, the powder is recovered by centrifugation (4000 rpm for 30 minutes).

The microcapsules obtained are characterized as being of reservoir type by observation with a scanning electron microscope.

EXAMPLE 6

Synthesis of Microcapsules Comprising 30% by Weight of Yellow No. 6 Aluminium Lake Relative to the Weight of the Polymer Matrix The synthetic protocol is identical to that described in Example 2, using 7.87 g of Yellow No. 6 aluminium lake (Sun Chemical) (instead of 0.18 g of D&C Red No. 7) and 2.4 g of alkyl benzoate so as to achieve an MDI/alkyl benzoate mass ratio=5).

The microcapsules obtained are characterized as being of reservoir type by observation with a scanning electron microscope.

EXAMPLE 7

Synthesis of Microcapsules Comprising 30% of Yellow No. 6 Aluminium Lake Relative to the Weight of the Polymer Matrix The synthetic protocol is identical to that described in Example 2, using 7.87 g of Yellow No. 6 aluminium lake (Sun Chemical) (instead of 0.18 g of D&C Red No. 7) and 12 g of alkyl benzoate (so as to achieve an MDI/alkyl benzoate mass ratio=1).

The microcapsules obtained are characterized as being of matrix type by observation with a scanning electron microscope.

EXAMPLE 8

Modification of the Shade of a Pigment as a Function of the Weight Content of Encapsulated Pigment Encapsulation of the pigment D&C Red No. 7 in a polymer matrix of polyurethane/polyurea type, performed using different weight contents of pigments as specified in Table 1 below, affords access to shades different from that of the initial pigment, and varying according to the content of encapsulated pigment.

The measurement of the shade is performed on 1.25 g of powder compacted at 100 bar in a crucible of dimensions h×l×w=0.3×2.5×2.2 and covered with a glass slide.

The colorimetric data are obtained in reflection on a Minolta spectrocolorimeter (D65/10' small aperture excluded specular component).

Table 1 below presents the calorimetric coordinates of D&C Red No. 7 according to its degree of encapsulation in microcapsules of polyurethane/polyurea type.

TABLE 1

| Pigment content | L* | a* | b* | c* | h° |
|---|---|---|---|---|---|
| 100% | 30.51 | 41.38 | 32.48 | 54.58 | 40.6 |
| 1% | 62.00 | 32.28 | 0.42 | 32.28 | 0.8 |
| 3% | 50.34 | 42.79 | 2.97 | 42.89 | 4.0 |
| 5% | 45.19 | 45.96 | 6.73 | 46.45 | 8.3 |
| 7% | 36.47 | 50.12 | 16.07 | 52.64 | 17.8 |
| 9% | 37.58 | 48.79 | 14.53 | 50.90 | 16.6 |
| 59% | 31.01 | 47.17 | 27.66 | 54.68 | 30.4 |

FIG. 1 is a graph of the values obtained.

The results show that the encapsulation according to the invention makes it possible to significantly broaden the colorimetric range relative to the original pigment, i.e. the pigment in its non-encapsulated form.

EXAMPLE 9

Comparison of the Running of Pure D&C Red No. 7 and of 5% Encapsulated D&C Red No. 7

D&C Red No. 7 in encapsulated form (according to the invention) or in non-encapsulated form (control) is placed in water containing 1% polysorbate (1686 M) and the solution is then centrifuged at 3000 rpm for 30 minutes.

The absorbance value of the material that has run is then determined for each of the two solutions (control and according to the invention) by measuring their optical density at a value of 535 nm. If necessary, the material that has run is diluted until an absorbance value of between 0 and 1 is obtained.

The running corresponds to the value of the optical density. Table 2 below presents the values obtained.

TABLE 2

| | Dilution factor | |
|---|---|---|
| | Per dilution | 1/16 |
| Pure DC Red 7 | 10.000 | 0.401 |
| 5% encapsulated DC Red 7 | 0.226 | |

It is found that encapsulation considerably reduces the running.

EXAMPLE 10

Lipstick Formulation

| | Mass % |
|---|---|
| Di-tert-butyl-4-hydroxytoluene | qs |
| Microcrystalline wax | 4 |
| Tridecyl trimellitate | 10 |
| Liquid lanolin | 9 |
| Diisostearyl malate | 13 |
| Protected acetyl lanolin | 9 |
| Lauric/palmitic/acetic/stearic acid triglycerides (50/20/10/10) | 5 |
| Protected isopropyl lanolate | 9 |
| 2-Octyldodecanol | qs 100 |
| 57% encapsulated D&C Red No. 7 (Example 5) | 10 |
| Phenyltrimethylsiloxytrisiloxane (viscosity: 20 cSt - MW: 372) | 4 |
| Polyethylene wax (MW: 500) | 8 |

The invention claimed is:

1. A cosmetic and/or dermatological composition for making up and/or caring for a keratin material, comprising:
   a physiologically acceptable medium, and
   least one composite dyestuff in the form of microcapsules consisting of
      a polymer matrix of crosslinked polyurethane, crosslinked polyurea and/or crosslinked polyurethane/polyurea obtained by interfacial polycondensation,
      a pigment selected from the group consisting of D&C pigment, FD&C pigment, lakes thereof and mixtures thereof and
      optionally at least one non-coloring substance chosen from cosmetic oils and waxes, vitamins, UV-screening agents, fragrances and moisturizers.

2. The composition according to claim 1, wherein the microcapsules are matrix microcapsules in which the polymer matrix is a continuous network and the pigment is dispersed in the continuous network.

3. The composition according to claim 1, wherein the non-coloring substance is present and is a cosmetic oil.

4. The composition according to claim 1, wherein the cosmetic oil is present and is isododecane or hydrogenated polyisobutylene.

5. The composition according to claim 1, wherein in the composite dyestuff, the pigment is at least partially organic, the microcapsules comprising from 10% to 80% by weight of the pigment relative to the weight of the polymer matrix.

6. The composition according to claim 1, wherein the microcapsules comprise from 30% to 60% by weight of the pigment relative to the weight of the polymer matrix.

7. The composition according to claim 1, wherein the composition comprises an additional ingredient selected from the group consisting of vitamins, thickeners, gelling agents, trace elements, softeners, sequestrants, fragrances, acidifying or basifying agents, preserving agents, sunscreens, surfactants, antioxidants, hair-loss counteractants, antidandruff agents, propellants, ceramides, cosmetic active agents, moisturizers, essential fatty acids, polymers, stabilizers and colloids, and mixtures thereof.

8. The composition according to claim 1, comprising from 0.01% to 50% by weight relative to its total weight, of the composite dyestuff.

9. The composition according to claim 1, comprising from 0.1% to 20% by weight relative to its total weight, of the composite dyestuff.

10. The composition according to claim 1, comprising from 0.5% to 15% by weight relative to its total weight, of the composite dyestuff.

11. The composition according to claim 1, wherein the composition is a hair dye composition.

12. The composition according to claim 1, wherein the composition is a makeup composition.

13. The composition according to claim 12, wherein the composition is a makeup composition for the nails or the lips.

14. A process for treating keratin materials, comprising applying the materials of the cosmetic composition as defined in claim 1.

* * * * *